(12) United States Patent
Roe et al.

(10) Patent No.: US 7,615,675 B2
(45) Date of Patent: *Nov. 10, 2009

(54) WEARABLE ARTICLE HAVING A TEMPERATURE CHANGE ELEMENT

(75) Inventors: Donald C. Roe, West Chester, OH (US); Patrick J. Allen, Cincinnati, OH (US); Edward P. Carlin, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 541 days.

This patent is subject to a terminal disclaimer.

(21) Appl. No.: 10/635,249

(22) Filed: Aug. 6, 2003

(65) Prior Publication Data

US 2004/0030310 A1 Feb. 12, 2004

Related U.S. Application Data

(63) Continuation of application No. 09/855,114, filed on May 14, 2001, now Pat. No. 6,642,427.

(51) Int. Cl.
*A61F 13/15* (2006.01)
*A61F 13/20* (2006.01)

(52) U.S. Cl. ............... 604/361; 604/364; 604/367

(58) Field of Classification Search ............ 604/361, 604/378, 385.01, 385.101, 385.24; 128/886; 116/205, 207
See application file for complete search history.

(56) References Cited

U.S. PATENT DOCUMENTS

| | | | |
|---|---|---|---|
| 2,043,325 A | 6/1936 | Jackson, Jr. |
| 3,794,024 A | 2/1974 | Kokx et al. |
| 3,860,003 A | 1/1975 | Buell |
| 3,927,673 A | 12/1975 | Taylor |
| 3,934,588 A | 1/1976 | Mesek et al. |
| 4,022,211 A | 5/1977 | Timmons et al. |
| 4,078,568 A | 3/1978 | Etes et al. |
| 4,106,001 A | 8/1978 | Mahoney |
| 4,140,115 A | 2/1979 | Schonfeld |
| 4,192,785 A | 3/1980 | Chen et al. |
| 4,231,369 A | 11/1980 | Sorensen et al. |
| 4,393,080 A | 7/1983 | Pawelchak et al. |
| 4,505,976 A | 3/1985 | Doehnert et al. |
| 4,551,490 A | 11/1985 | Doyle et al. |
| 4,593,053 A | 6/1986 | Jevne et al. |

(Continued)

FOREIGN PATENT DOCUMENTS

EP 0 119 919 9/1984

(Continued)

OTHER PUBLICATIONS

U.S. Appl. No. 11/703,393, filed Feb. 06, 2007, Office Action dated Jun. 24, 2009.

*Primary Examiner*—Michele Kidwell
(74) *Attorney, Agent, or Firm*—Charles R. Matson; Matthew P. Fitzpatrick

(57) ABSTRACT

A wearable article useful for facilitating toilet training. The wearable article includes a temperature change element providing a cool/wet signal when wetted which causes discomfort to the wearer. The temperature change element comprises a temperature change substance disposed on an impermeable material in order to maximize the thermal signal provided to the skin of the wearer.

5 Claims, 10 Drawing Sheets

U.S. PATENT DOCUMENTS

| | | | |
|---|---|---|---|
| 4,657,538 A | | 4/1987 | Becker et al. |
| 4,699,146 A | | 10/1987 | Sieverding |
| 4,738,257 A | | 4/1988 | Meyer et al. |
| 4,768,503 A | | 9/1988 | Highgate et al. |
| 4,778,459 A | | 10/1988 | Fuisz |
| 4,892,536 A | | 1/1990 | DesMarais et al. |
| 4,990,147 A | * | 2/1991 | Freeland ............... 604/385.22 |
| 5,037,416 A | | 8/1991 | Allen et al. |
| 5,062,839 A | * | 11/1991 | Anderson ............. 604/385.21 |
| 5,151,092 A | | 9/1992 | Buell et al. |
| 5,167,655 A | * | 12/1992 | McCoy ....................... 604/396 |
| 5,178,139 A | * | 1/1993 | Angelillo et al. ............. 607/114 |
| 5,236,428 A | * | 8/1993 | Zajaczkowski ......... 604/385.26 |
| 5,266,592 A | | 11/1993 | Grub et al. |
| 5,269,775 A | | 12/1993 | Freeland et al. |
| 5,277,180 A | | 1/1994 | Angelillo et al. |
| 5,342,343 A | | 8/1994 | Kitaoka et al. |
| 5,614,586 A | | 3/1997 | Tang et al. |
| 5,649,914 A | | 7/1997 | Glaug et al. |
| 5,658,268 A | | 8/1997 | Johns et al. |
| 5,674,275 A | | 10/1997 | Tang et al. |
| 5,681,298 A | | 10/1997 | Brunner et al. |
| 5,702,376 A | | 12/1997 | Glaug et al. |
| 5,726,260 A | | 3/1998 | Derleth et al. |
| 5,728,125 A | | 3/1998 | Salinas |
| 5,797,892 A | | 8/1998 | Glaug et al. |
| 5,846,230 A | | 12/1998 | Osborn, III et al. |
| 5,879,378 A | * | 3/1999 | Usui ......................... 607/96 |
| 5,885,264 A | | 3/1999 | Matsushita |
| 5,891,124 A | | 4/1999 | Nomura et al. |
| 5,947,947 A | | 9/1999 | Tanzer et al. |
| 6,114,597 A | | 9/2000 | Romare |
| 6,146,367 A | | 11/2000 | Otsubo et al. |
| 6,160,200 A | | 12/2000 | Ehrnsperger et al. |
| 6,169,225 B1 | | 1/2001 | Otsubo |
| 6,200,668 B1 | | 3/2001 | Kronzer |
| 6,229,063 B1 | | 5/2001 | Shimoe et al. |
| 6,297,424 B1 | | 10/2001 | Olson et al. |
| 6,307,119 B1 | | 10/2001 | Cammarota et al. |
| 6,320,096 B1 | | 11/2001 | Inoue et al. |
| 6,428,526 B1 | | 8/2002 | Heindel et al. |
| 6,436,128 B1 | * | 8/2002 | Usui ......................... 607/96 |
| 6,482,191 B1 | | 11/2002 | Roe et al. |
| 6,515,194 B2 | | 2/2003 | Neading et al. |
| 6,627,786 B2 | * | 9/2003 | Roe et al. .................... 604/361 |
| 6,635,797 B2 | | 10/2003 | Olson et al. |
| 6,642,427 B2 | | 11/2003 | Roe et al. |
| 6,645,190 B1 | | 11/2003 | Olson et al. |
| 6,657,099 B1 | * | 12/2003 | Underhill et al. ........... 604/361 |
| 6,710,221 B1 | | 3/2004 | Pierce et al. |
| 6,726,668 B2 | | 4/2004 | Underhill et al. |
| 6,791,004 B2 | * | 9/2004 | Sprengard-Eichel et al. 604/361 |
| 6,793,649 B1 | | 9/2004 | Fujioka et al. |
| 6,927,316 B1 | * | 8/2005 | Faries et al. ................... 602/43 |
| 2001/0049513 A1 | | 12/2001 | Neading et al. |
| 2002/0143316 A1 | | 10/2002 | Sherrod et al. |
| 2002/0169427 A1 | | 11/2002 | Roe et al. |
| 2003/0060794 A1 | | 3/2003 | Olson |
| 2003/0100872 A1 | | 5/2003 | Roe et al. |
| 2003/0114807 A1 | | 6/2003 | Underhill et al. |
| 2003/0114821 A1 | | 6/2003 | Underhill et al. |
| 2003/0135184 A1 | | 7/2003 | Van Gompel et al. |
| 2003/0155255 A1 | | 8/2003 | Yahalom et al. |
| 2003/0155265 A1 | | 8/2003 | Tippey |
| 2003/0199845 A1 | | 10/2003 | Roe et al. |
| 2004/0199133 A1 | | 10/2004 | Underhill et al. |
| 2004/0220540 A1 | | 11/2004 | Underhill et al. |
| 2005/0096612 A1 | | 5/2005 | Davis et al. |
| 2005/0148961 A1 | | 7/2005 | Sosalla et al. |
| 2008/0065034 A1 | | 3/2008 | Vargo et al. |

FOREIGN PATENT DOCUMENTS

| | | |
|---|---|---|
| EP | 0 861 645 | 9/1998 |
| EP | 0 904 758 | 3/1999 |
| EP | 0 919 213 | 6/1999 |
| GB | 2 244 201 A * | 11/1991 |
| WO | WO 94/013235 | 6/1994 |
| WO | WO 96/12459 A2 | 5/1996 |
| WO | WO 02/091968 A3 * | 11/2002 |
| WO | WO 05/016202 | 2/2005 |

* cited by examiner

WEARABLE ARTICLE HAVING A TEMPERATURE CHANGE ELEMENT

CROSS-REFERENCE TO RELATED APPLICATION

This application is a continuation of commonly assigned U.S. application Ser. No. 09/855,114 filed 14 May 2001 now U.S. Pat. No. 6,642,427 in the name of Donald C. Roe et al., confirmation number 8750.

FIELD OF THE INVENTION

This invention is directed to hygienic absorbent articles, such as diapers, training pants and the like. Particularly, the invention is directed to training pants facilitating the toilet training process.

BACKGROUND OF THE INVENTION

Absorbent articles are well known in the art. These articles typically have an absorbent core held or positioned in proximity to the body of a wearer during use by a fastening system in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. The disposable diapers typically comprise a single design available in different sizes to fit a variety of wearers ranging from newborns to toddlers undergoing, toilet training. The design of the diaper typically affects performance, such as, ability to absorb and contain bodily waste. The size of the diaper typically affects fit, for example, the size of the diaper waist opening, the size of the openings around the thighs, and the length or "pitch" of the diaper.

The toilet training stage may be referred to as the "point of exit" as toddlers typically leave the product category once training is successfully completed. The age at which children are toilet trained in "developed" countries has increased steadily over the past several decades and is now in the range of about 24-42 months. One reason toilet training has become delayed is due to significant technical improvements in diaper dryness and comfort. In modern diapers, the child has dry skin even after one or more urinations. As a result, the child feels little or no discomfort and often may not even be aware that they have urinated.

Many parents have the child wear cotton training pants or underwear during toilet training so the child feels discomfort following urination in their "pants". It is believed that such discomfort assists with learning or provides motivation to learn proper toilet training. Cotton training pants leave the skin wet and, due to their high breathability, promote evaporative cooling of the skin, further enhancing discomfort. The current tradeoff in this approach, however, is that cotton training pants have poor urine containment leading to wet clothing and often times, wet surroundings e.g. carpeting, furniture, etc. Clearly there is a need to provide a training signal to the toilet training child while preventing urine leakage and unnecessary changes of clothing.

A number of attempts to address this need have been made in the art. One attempt U.S. Pat. No. 5,681,298) involves the use of a liquid permeable temperature change member to provide a thermal signal to the child. The temperature change member comprises salts having positive (exothermic) or negative (endothermic) heats of solution in water and is disposed with the absorbent assembly. A key requirement is that the total energy change per unit area be about 6 to about 30 cal/cm$^2$. This approach has several critical limitations. First, the liquid permeability of the temperature change member allows the salt to be dissolved and washed into the absorbent assembly, away from the skin of the wearer, significantly reducing the opportunity to provide a thermal signal to the skin. Additionally, the attempt to overcome this phenomenon via the requirement of the 6-30 cal/cm$^2$ total energy change involves the use of significant quantities of the salt, increasing the cost and complexity of the product.

Thus, it would be desirable to provide a wearable article that can facilitate toilet training by providing an effective signal notifying the wearer by causing discomfort when a discharge of bodily waste has occurred while at the same time providing the protection of an absorbent article, preventing soiling of the wearer's clothing and surroundings. Particularly, it would be desirable to provide such a wearable article providing an effective thermal signal of urination using minimal amounts of endothermic or exothermic salt. Further it would be desirable to provide a thermal signal of urination with less than about 3 cal/cm$^2$ total energy change.

SUMMARY OF THE INVENTION

In order to solve one or more of the problems found in the art, a wearable article, such as an absorbent article, is provided with a temperature change element producing a temperature change that is sensed by the skin of the wearer, signaling the wearer that a discharge of bodily exudates, such as urine, has occurred. The temperature change element comprises a permeable layer and an impermeable layer opposite the permeable layer. In certain embodiments, the permeable layer faces the body of the wearer and the impermeable layer faces the absorbent assembly of the wearable article. A temperature change substance, such as an endothermic salt, is interposed between the permeable layer and the impermeable layer.

Once a wearer urinates wetting a target area of the temperature change element aligned with the wearer's urethra, the permeable layer enables the urine to penetrate through the thickness of the layer in the z-direction. The impermeable layer disposed opposite the permeable layer is not penetrative by the urine in the z direction thereby minimizing the temperature change substance and/or cooled urine from being washed away from the skin of the wearer and into the absorbent assembly or other underlying layers. In addition, the impermeable layer provides a path of least resistance for the movement of fluid between the permeable layer and the impermeable layer in the x-y plane thereby enhancing the amount of temperature change substance wetted therebetween. As a result, urine is able to move into areas of the temperature change element adjacent to the target area thereby increasing the effectiveness of the signal provided by the temperature change element.

Furthermore, since the urine passing through the permeable layer in the z direction does not pass through the impermeable layer into the underlying layers of the article, the temperature change element of the present invention can be made to produce an effective signal utilizing minimal quantities of the temperature change substance. Also, even though temperature change element of the present invention can be made to produce a total unit area energy change ranging from 0.5 cal/cm$^2$ to about 30 cal/cm$^2$, since the permeable layer is held in contact with the wearer's skin, the wearer feels not only a temperature change effect resulting from an insult of urine but also wetness. Consequently, the temperature change element of the present invention is capable of producing an effective signal at a reduced total unit area energy change ranging from about 0.5 cal/cm$^2$ to about 5.0 cal/cm$^2$.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 6b is a cross sectional view of the diaper illustrated in FIG. 6a.

FIG. 7b is a cross sectional view of the diaper illustrated in FIG. 7a.

FIG. 8b is a cross sectional view of the diaper illustrated in FIG. 8a.

FIG. 9b is a cross sectional view of the diaper illustrated in FIG. 9a.

FIG. 10b is a cross sectional view of the diaper illustrated in FIG. 10a.

DETAILED DESCRIPTION OF THE INVENTION

Figure 1:
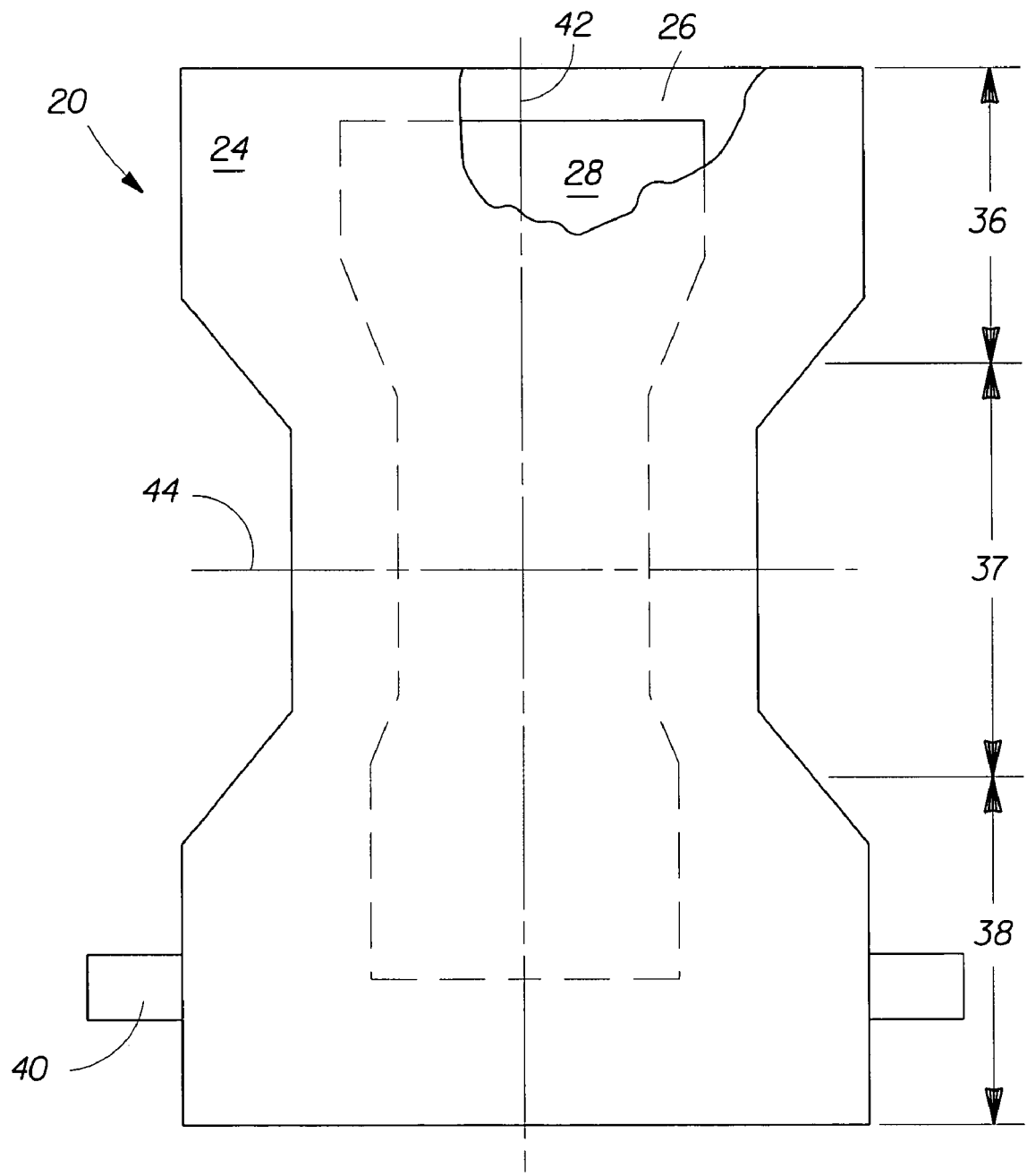
FIG. 1 is a plan view of a disposable diaper.

While this specification concludes with claims particularly pointing out and distinctly claiming that which is regarded as the invention, it is anticipated that the invention can be more readily understood through reading the following detailed description of the invention and study of the included drawings.

The present invention provides a wearable article having a temperature change element that provides a change in temperature that is sensed by the skin of the wearer once the temperature change element becomes wetted with exudates discharged from the body of the wearer. The temperature change element is equally applicable to wearable articles such as disposable absorbent articles including training pants, incontinence briefs, incontinence undergarments, absorbent inserts, diaper holders and liners, feminine hygiene garments, and the like. One embodiment of an absorbent article of the present invention is a unitary disposable absorbent article, such as the disposable diaper 20, shown in FIG. 1. However, preferably, the present invention is applicable to disposable training pants and pull-on diapers designed to facilitate toilet training.

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "impermeable" generally refers to articles and/or elements that are not penetrative by fluid through the entire Z-directional thickness of the article under pressure of 0.14 lb/in$^2$ or less. Preferably, the impermeable article or element is not penetrative by fluid under pressures of 0.5 lb/in$^2$ or less. More preferably, the impermeable article or element is not penetrative by fluid under pressures of 1.0 lb/in$^2$ or less.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. The diaper 20 includes a longitudinal axis 42 and a transverse axis 44. One end portion 36 of the diaper 20 is configured as a first waist region of the diaper 20. The opposite end portion 38 is configured as a second waist region of the diaper 20. An intermediate portion 37 of the diaper 20 is configured as a crotch region, which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The diaper 20 preferably comprises a liquid pervious topsheet 24, a liquid impervious backsheet 26, and an absorbent core 28 encased between the topsheet 24 and the backsheet 26. The topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The diaper 20 may include a fastener such as a hook and loop type fastening system 40 including at least one engaging component (male fastening component) and at least one landing zone (female fastening component). The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. Nos. 3,860,003; and 5,151,092, which are incorporated by reference herein.

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

Figure 2:
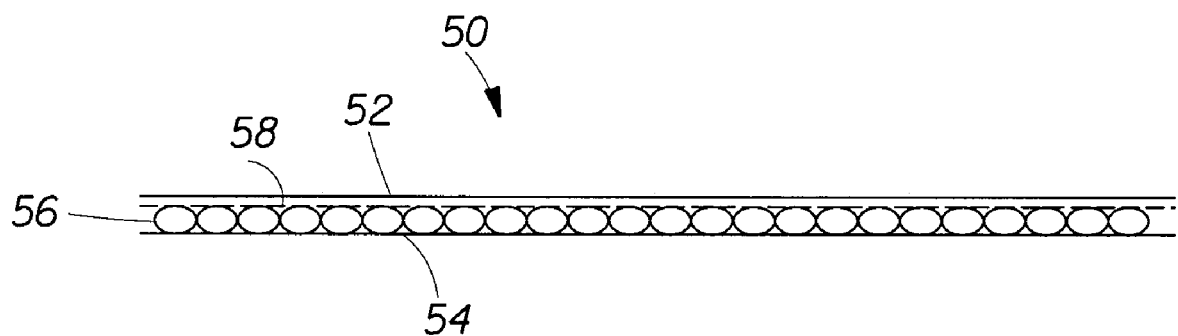
FIG. 2 is a cross sectional view of a temperature change element according to the present invention.

An exemplary temperature change element according to the present invention is shown in FIG. 2. The temperature change element 50 comprises a permeable layer 52, an impermeable layer 54, disposed opposite the permeable layer 52, and a temperature change substance 56 disposed on the permeable layer. Preferably, the temperature change substance 56 is interposed between the permeable layer 52 and the impermeable layer 54 as shown in FIG. 2, however, embodiments are contemplated where the temperature change substance is disposed on the permeable layer on a surface opposite the impermeable layer. The temperature change element 50 according to the present invention preferably comprises a permeable body-facing layer (upper layer) and an impermeable layer (lower layer) opposite the body facing layer. Alternatively, however, the temperature change element according to the present invention may comprise an impermeable body-facing layer (upper layer) and a permeable layer (lower layer) opposite the body facing layer. For this latter embodiment, the wetting of the temperature change substance is accomplished through wicking. Exemplary embodiments are described below.

The temperature change substance 56 provides a signal to the wearer in the form of a temperature change when placed near the wearer and contacted with urine. The temperature change substance 56 may be in the form of particles. However, alternatively, the temperature change substance 56 may be disposed on one of the two layers in the form of a coating. For example, the temperature change substance may be deposited on the permeable layer by wetting the layer with a saturated aqueous solution of the temperature change substance and subsequently evaporating the water via drying.

During insults of urine, the permeable layer 52 allows urine to penetrate in the z-direction and also provides a medium for the flow of urine in the x-y plane via wicking. The combination of penetration and flow provides the urine access to the temperature change substance 56. The urine dissolves the temperature change substance resulting in a significant decrease/increase in the temperature of the urine. The layer opposite the permeable layer is impermeable, as defined herein, so as to prevent the liquid (the temperature change substance/urine solution) from migrating to the underlying layers of the absorbent structure. The impermeable layer also supports the flow of liquid between the permeable and impermeable layers and retains the liquid in as intimate and continuous contact as possible with the wearer's body in order to maximize the temperature change signal perceived by the wearer.

The temperature change element 50 may also include a transition layer 58 between the permeable layer 52 and the impermeable layer 54, separating the temperature change substance 56 from the permeable layer 52. The transition layer 58 may comprise a cellulose layer, a tissue layer, a nonwoven layer, a foam layer or any other layer that can aid in holding the temperature change substance 56 in place during manufacturing and during use, as well as prevent the temperature change substance 56 from contacting the wearer's skin. In addition, the transition layer may enhance wicking, thereby increasing the area wetted on the temperature change element 50 resulting in a more effective signal.

The temperature change may involve either absorption or release of heat to change the temperature of the surroundings to a point noticeable to the wearer. For temperature change substances that produce a temperature change when dissolved in water, the energy change is known as the "heat of solution". Temperature change substances having a negative heat of solution involve absorption of heat and a decrease in temperature and are known as endothermic substances. Endothermic substances provide the wearer with a cool sensation. Temperature change substances having a positive heat of solution involve the release of heat and an increase in temperature and are known as exothermic substances. Exothermic substances provide the wearer with a warm sensation.

The temperature change substance is responsive to contact with an aqueous solution such as urine to either absorb or release heat. The mechanism by which this is accomplished is the dissolution of the substance in the aqueous solution, the swelling of the substance in the aqueous solution, or the reaction of one or more substances in the aqueous solution. In particular embodiments, the temperature change substance is a material which has a substantial energy difference between a dissolved state and a crystalline state, so that energy in the form of heat is absorbed or released to the environment upon contact with, and dissolution in, water or urine, as described above.

While a wide variety of substances may result in a temperature change when contacted with an aqueous solution, the selection of a particular temperature change substance and the determination of the amount to be used should be based in part on the desired temperature change. While the temperature change substance disposed in the temperature change element may be an endothermic or exothermic, an endothermic substance is preferred in certain embodiments as it more closely simulates the cooling signal delivered to the wearer by traditional cotton training pants. In addition, exothermic substances do not provide as good a signal since the wearer is generally used to the warm environment provided by the diaper. Further, a heated environment promotes bacterial growth and the corresponding diaper rash attributed to bacteria and fungi.

Typically, the urine touching the skin should be at 27 deg C. or lower for the wearer to readily perceive the signal and/or discomfort. Preferably, the urine accessible to the skin is cooled to about 25 deg C. to maximize the perceived signal. Most preferably, the urine accessible to the skin is cooled to about 22 deg C. or lower to maximize the perceived signal. To achieve this result, the specific temperature change substance employed, the amount used, and the location of the substance should be selected to produce the required total energy change upon urination by the wearer. The total unit area energy change in the temperature change element upon urination is typically greater than about 0.05 cal/cm$^2$. More typically, the total unit area energy change is in the range of about 0.05 cal/cm$^2$ to about 30 cal/cm$^2$. The magnitude of the total unit area energy values disclosed herein are absolute values and therefore, equally apply to negative heat of solution (endothermic) values and positive heat of solution (exothermic) values.

Since the impermeable layer of the temperature change element of the present invention retains the cooled liquid in a location accessible to the skin, a smaller total unit area energy change may be required to provide an effective signal. For instance, in certain embodiments of the present invention, the total unit area energy change in the temperature change element can be less than about 5 cal/cm$^2$. In other embodiments, the total unit area energy change can be less than about 3 cal/cm$^2$, less than about 2 cal/cm$^2$, or even less than about 1.5 cal/cm$^2$. In any event, the total unit area energy change provided by the temperature change element of the present invention can be between about 0.05 cal/cm$^2$ and about 30 cal/cm$^2$, between about 0.05 cal/cm$^2$ and about 5 cal/cm$^2$, between about 0.075 cal/cm$^2$ and about 4.5 cal/cm$^2$, or even between about 1.0 cal/cm$^2$ and 3.0 cal/cm$^2$.

By way of example, potassium chloride (KCl) may be selected as the temperature change substance. KCl is capable of providing a cooling sensation when saturated, because KCl particles absorb heat, i.e., are endothermic, when dissolved in an aqueous solution. KCl has a heat of solution of approximately −59 calories per gram (cal/g). A desirable add-on amount of potassium chloride particles would be a basis weight of about 0.023 grams per square centimeter (g/cm$^2$). The selection of potassium chloride particles at this basis weight results in a possible total energy change of −59 cal/g× 0.023 g/cm$^2$ which equals −1.36 cal/cm$^2$.

Temperature change substances which absorb or release heat on contact with an aqueous solution desirably have a heat of solution, hydration, or reaction greater than about 40 cal/g or less than about −40 cal/g. The heat of solution, hydration, or reaction is suitably within the range of from about 40 to about 90 cal/g or from about −40 to about −90 cal/g, and more particularly from about 50 to about 70 cal/g or from about −50 to about −70 cal/g, such as KCl at −59 cal/g. Typical basis weights for such temperature change substances range from about 0.001 to about 0.075 g/cm2, and more particularly from about 0.01 to about 0.05 g/cm2.

As referenced above, temperature change substances suitable for use in disposable diapers 20 and training pants include those that dissolve in an aqueous solution. The solubility of such temperature change substances is typically from about 1.0 to about 15 grams of water ($H_2O$) per gram of material (g/g), and more particularly from about 3 to about 7 g/g for improved performance. The solubility range for potassium chloride (KCl), referenced above, for 14% to 28% saturation is about 6.0 to about 2.6 grams of $H_2O$ per grams of potassium chloride.

Suitable temperature change substances that absorb heat during dissolution can comprise endothermic salts which include salt hydrates, such as sodium acetate ($H_2O$), sodium carbonate (10$H_2O$), sodium sulfate (10$H_2O$), sodium thiosulfate (5$H_2O$), and sodium phosphate (10$H_2O$); anhydrous salts, such as ammonium nitrate, potassium nitrate, ammonium chloride, potassium chloride, and sodium nitrate; organic compounds, such as urea, xylitol, and other sugars; or the like. Temperature change substances that release heat during the dissolution comprise exothermic salts and can include aluminum chloride, aluminum sulfate, potassium aluminum sulfate, or the like. The temperature change substance may also include those substances that absorb or release heat during swelling. By way of illustration, one suitable temperature change substance that releases heat during swelling is a lightly cross-linked partially neutralized polyacrylic acid.

Alternatively, the temperature change substance may include those substances that absorb or release heat upon reaction with an aqueous solution. Examples include ortho esters or ketals such as menthone ketals which result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued Sep. 20, 1994, to Greenberg; and U.S. Pat. No. 5,266,592 issued Nov. 30, 1993, to Grub et al.; which are incorporated herein by reference.

The temperature change substance is desirably, although not necessarily, in the form of particles sandwiched between the permeable layer and the impermeable layer. Exemplary permeable layers suitable for use in the temperature change elements of the present invention include nonwovens, foams, woven materials, etc. The permeable layer is preferably hydrophilic and capable of retaining at least 4-12 g/g urine against gravity. Exemplary impermeable layers suitable for use in the temperature change elements of the present invention include polyolefinic films, microporous or breathable films, other films, and hydrophobic nonwovens having a hydrohead greater than about 0.14 lb/in$^2$. Suitable hydrophobic nonwovens include SM (spunbond meltblown), SMS (spunbond meltblown spunbond), and SMMS (spunbond meltblown meltblown spunbond) composites.

The temperature change substance interposed between the permeable and impermeable layers may be discretely disposed in areas near to a point of discharge on the wearer or uniformly dispersed throughout the temperature change element. The point of discharge is typically flooded during an insult of urine causing the temperature change substances in the area to become quickly over saturated, providing little, if any, temperature change effect. However, the areas adjacent to the point of discharge are less saturated since they are wetted via wicking and the flow of urine in the x-y plane resulting in a prominent temperature change signal to the wearer. In any event, the temperature change effect is most predominate following a single urination incident.

Figure 3:
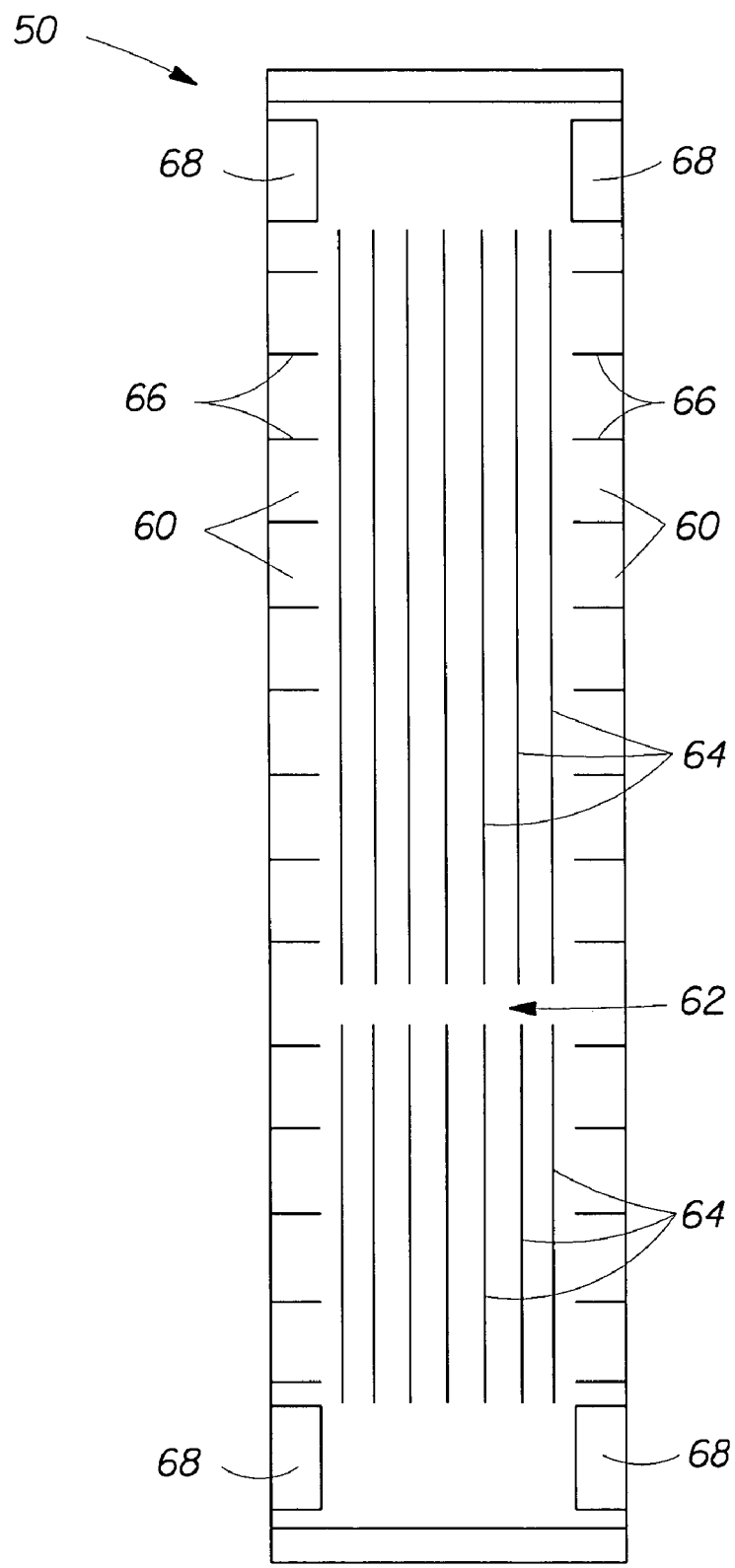
FIG. 3 is a plan view an embodiment of the temperature change element according to the present invention.

In an embodiment shown in FIG. 3, the temperature change substance is desirably accumulated in a plurality of compartments 60 disposed along the longitudinal edges of the temperature change element 50. For this embodiment, the temperature change element 50 includes a urine acquisition zone 62 and wicking channels 64. The wicking channels 64 move fluid in parallel to multiple temperature change substance-containing compartments 60 in order to minimize the risk of over saturation. Each of the compartments 60 containing the temperature change substance may be separated from one another via bond lines 66. The bond lines 66 prevent the urine/temperature change substance solution from flowing to subsequent compartments 60 and reaching an over saturation level. These bond lines 66 may be formed using adhesives, ultrasonic bonds, radio frequency bonds, or other suitable means. This configuration may provide multiple urination signals corresponding to multiple incidents of urination. Further, the temperature change element may include elastic elements that enable the temperature change element to deflect towards the wearer's skin during use. As shown in FIG. 3, elastic elements 68 may be disposed near the ends of the element 50.

The temperature change element according to the present invention may be arranged in an absorbent article in a variety of configurations. In addition, absorbent articles may include a single temperature change element or a plurality of temperature change elements. In any event, the temperature change element(s) are preferably a part of, or attached to, an element or web, such as a topsheet, which is reliably held against the skin of the wearer. In addition, the temperature change element(s) are preferably positioned within the absorbent article to enhance the likelihood of being wetted with urine.

Figure 4A:
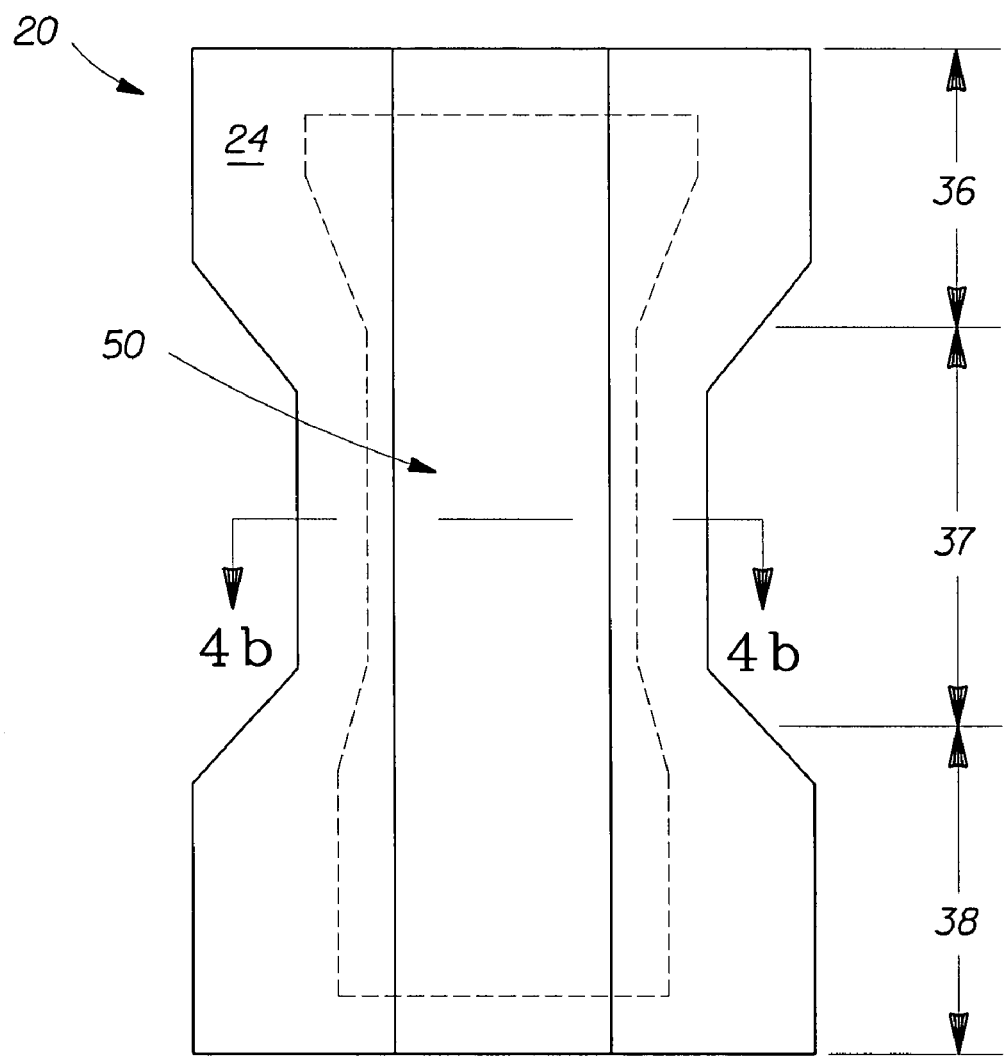
FIG. 4a is a plan view of a diaper having a temperature change element disposed on a body-facing surface.
Figure 4B:
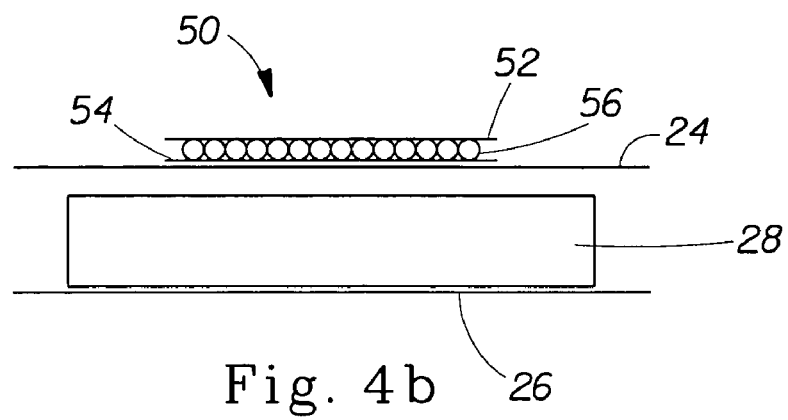
FIG. 4b is a cross sectional view of the diaper shown in FIG. 4a illustrating the layers of the temperature change element.

An exemplary embodiment of a temperature change element 50 disposed with the topsheet 24 is illustrated in FIGS. 4a and 4b. As shown, the temperature change element 50 comprises a separate composite member attached to the topsheet 24. The temperature change element 50 comprises a permeable 52 body-facing layer, and impermeable layer 54 opposite the body-facing layer and a temperature change substance 56 interposed therebetween. For this embodiment, the temperature change element 50 is preferably configured and assembled to enhance the likelihood of making contact with the wearer's skin during use. For instance, the impermeable layer 54 of the temperature change element 50 may be bonded to the topsheet 24 using adhesives, ultrasonic bonds, radio frequency bonds, or other suitable means while either the topsheet 24 or the temperature change element 50 is elastically foreshortened to deflect the element 50 towards the wearer's skin.

Figure 5:
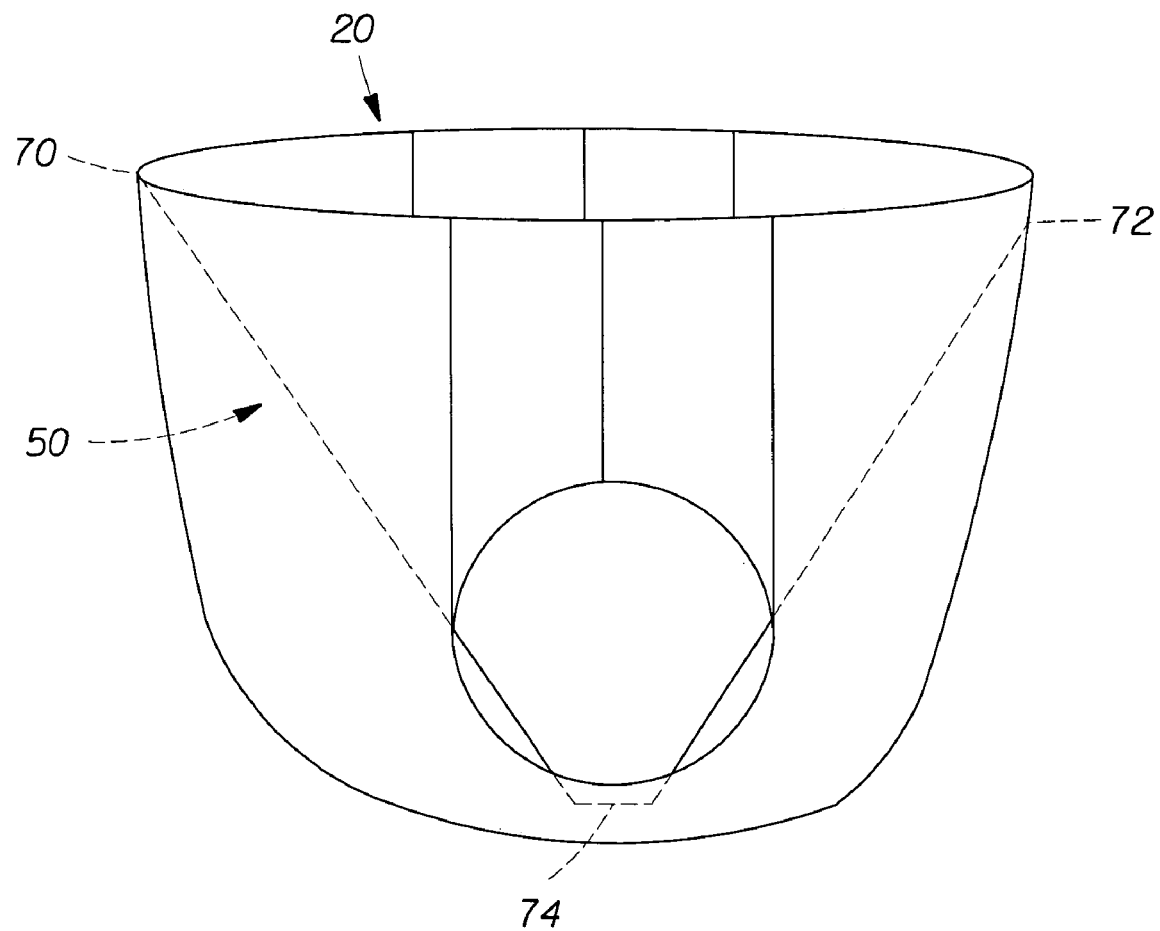
FIG. 5 is an isometric view of a pull-on diaper illustrating the attachment of the temperature change element.

In an embodiment illustrated in FIG. 5, a temperature change element 50 comprising a separate composite member is disposed on the topsheet 24 of a pull-on type diaper. For this embodiment, the temperature change element 50 has elastic properties and includes a first longitudinal end 70 attached to the first waist region 36 and a second longitudinal end 72 attached to the second waist region 38. In addition, a center portion 74 of the element 50 is preferably attached to the crotch region 37 of the diaper 20 in order to stabilize the element and facilitate fitting the article to the wearer, prevent interference with bowel movements and ensure good contact with the wearer's skin.

Figure 6A:
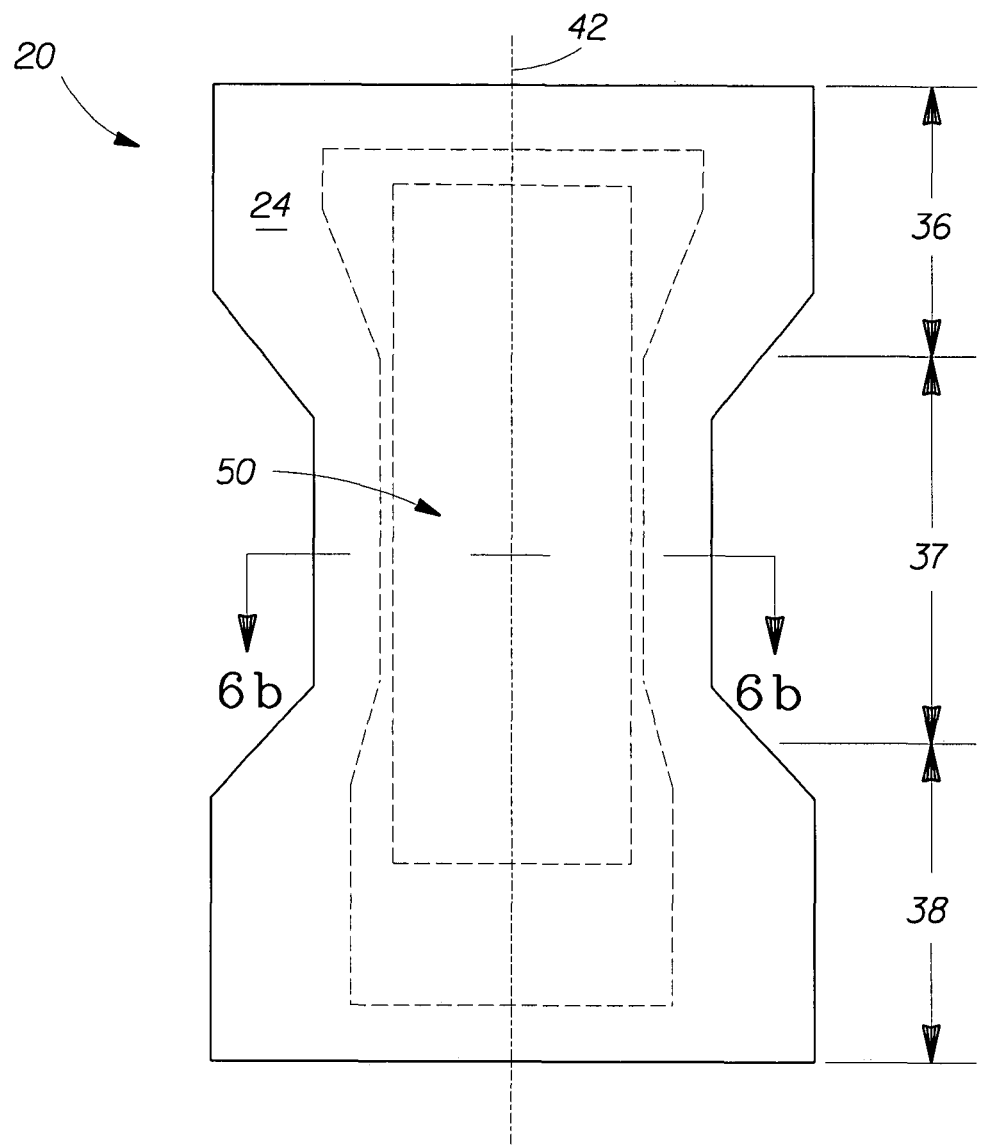
FIG. 6a is a plan view of a diaper having a temperature change element integrated with the topsheet.
Figure 6B:
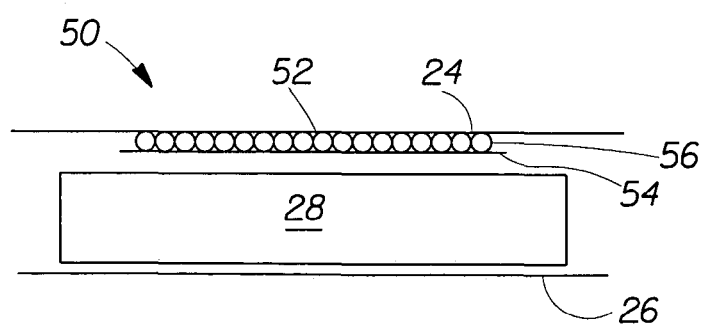

In an alternate embodiment shown in FIGS. 6a and 6b, the impermeable layer 54 of the temperature change element 50 is attached to the inner surface of the topsheet 24 such that at least a portion of the topsheet 24 forms the permeable layer 52 of the temperature change element 50, sandwiching the temperature change substance 56 between the impermeable layer 54 and the topsheet 24. For this embodiment, the topsheet 24 is preferably elastically foreshortened to deflect the temperature change element 50 into contact with the wearer's skin. Alternatively, this embodiment may include a topsheet that is shorter in length than the backsheet, having the longitudinal ends of the topsheet contiguous with the longitudinal ends of the backsheet so that as the diaper is fitted around the wearer, the topsheet is forced into contact with the wearer's skin.

Regardless of the specific construction, the position and/or structure of the temperature change element 50 should enable the temperature change substance to be wetted with urine and thereafter held in contact with the wearer's skin. The temperature change element is preferably disposed in at least a portion of the crotch region 37 of the diaper 20, centered about the longitudinal centerline 42. The temperature change element 50 may extend over a portion of the disposable absorbent article spanning less than one half of the length of the article or else extend a substantial part of the article spanning more than one half the length of the article. Furthermore, the temperature change element 50 is preferably coordinated with the wearer's urethra in order to cover the area in which urine initiates contact with the disposable absorbent article.

Figure 7A:
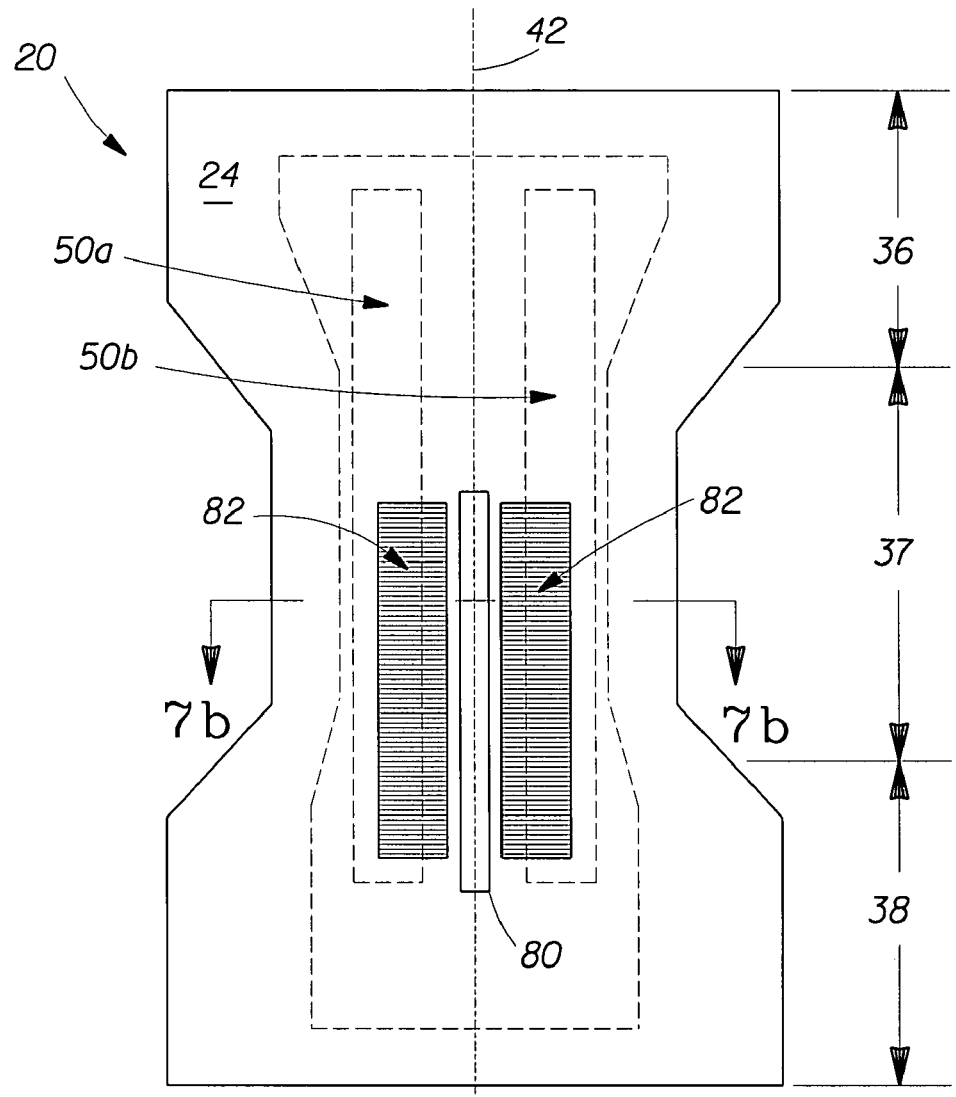
FIG. 7a is a plan view of a diaper having two temperature change elements integrated with the topsheet and disposed parallel to and spaced apart from the longitudinal axis with an elongated slit opening interposed therebetween.
Figure 7B:
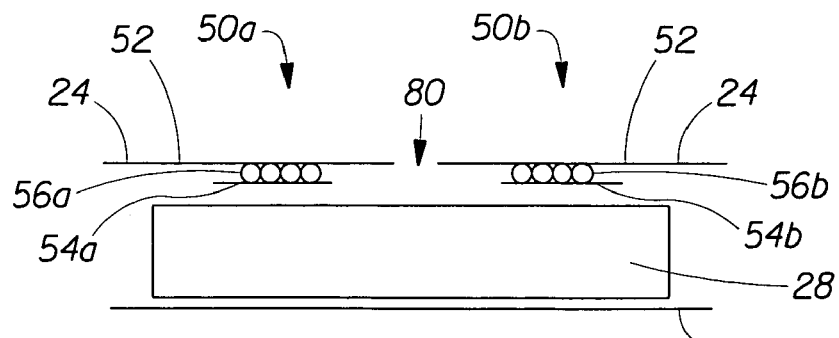

An embodiment providing a plurality of temperature change elements is shown in FIGS. 7a and 7b. Two impermeable layers 54a, 54b, are attached to the bottom surface of the topsheet 24 forming two the temperature change elements 50a, 50b. For this embodiment, the temperature change substance 56a and 56b is disposed between the topsheet and the impermeable layers 54a, 54b so that the topsheet forms the permeable layers 52 of the temperature change elements. The two impermeable layers 54a, 54b are disposed parallel to and spaced apart from the longitudinal centerline 42 of the diaper 20. The impermeable layers 54a, 54b are bonded to the lower side of the topsheet 24 along the longitudinal and transverse edges of the impermeable material using adhesives, ultrasonic bonds, radio frequency bonds, or other suitable means.

As shown in FIGS. 7a and 7b the spacing of the impermeable layers provide room for an elongated slit opening 80 in the topsheet 24. The elongated slit opening 80 is adapted to receive feces from the wearer and isolate the same from the wearer's skin. As shown, the slit opening 80 is preferably interposed between the temperature change elements 50a, 50b along the longitudinal centerline 42 of the diaper 20. Elasticized regions 82 located adjacent to the slit opening 80 maintain alignment of the slit opening 80 with the wearer's anus during use. The elasticized regions 82 may also deflect the temperature change elements 50a, 50b towards the wearer's skin to maintain contact therewith during use. Exemplary elasticized topsheets including elongated slit openings are disclosed in U.S. patent application Ser. No. 09/694,751, which is incorporated herein by reference. Alternatively, the impermeable layers 54a, 54b of the temperature change elements 50a, 50b may be elastically foreshortened to provide benefits of the elasticized regions 82 disposed in the topsheet 24.

Figure 8A:
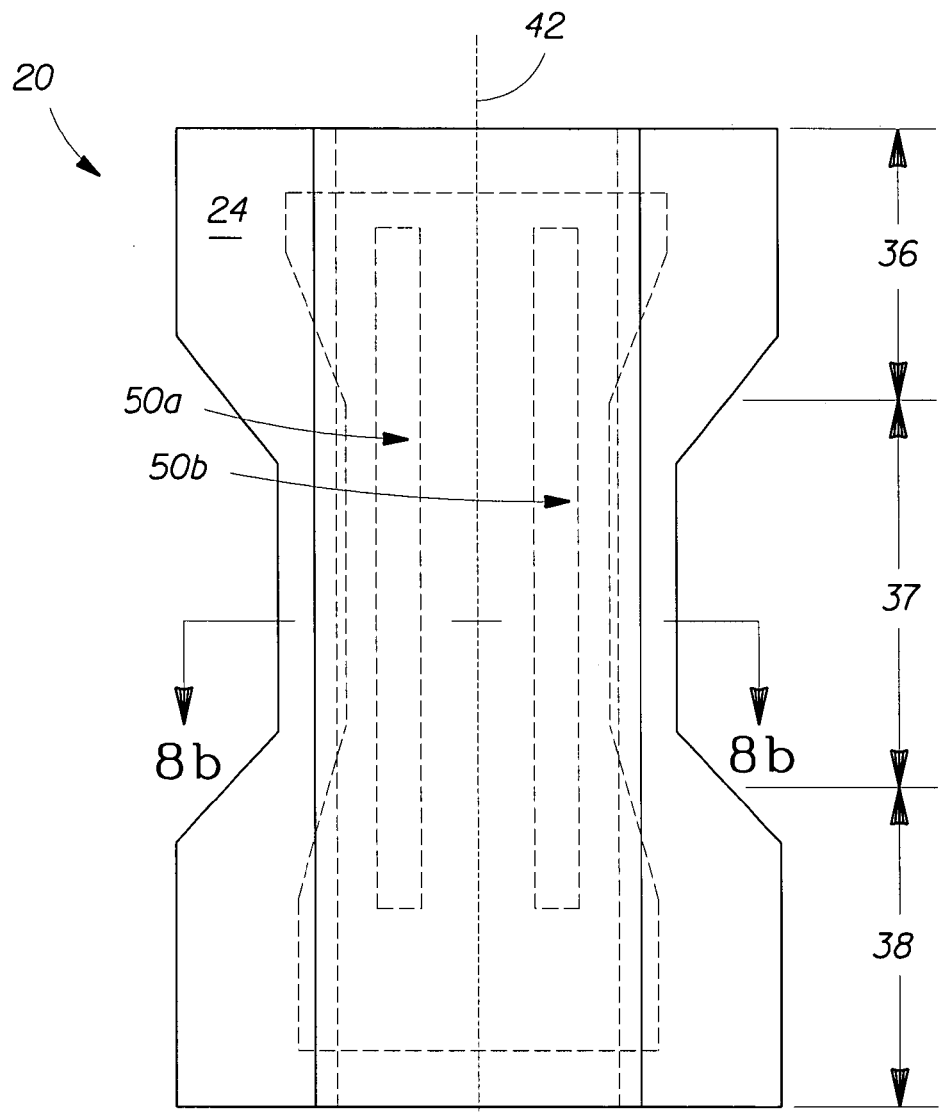
FIG. 8a is a plan view of a diaper having a Z-folded topsheet with two temperature change elements disposed in the Z-folds in the topsheet.
Figure 8B:
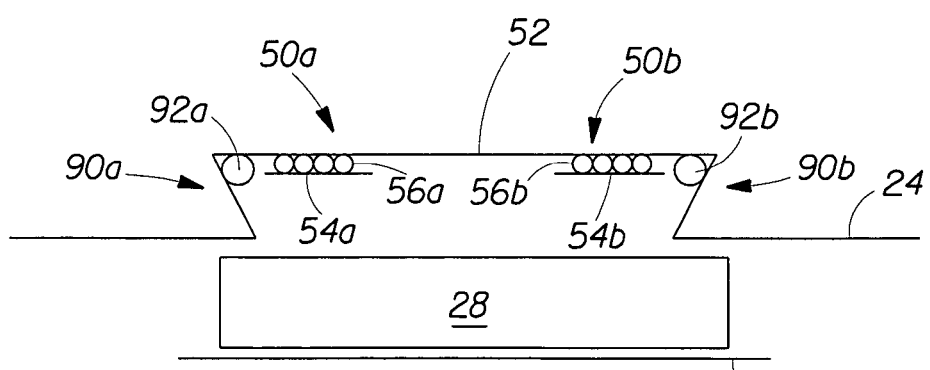

In another alternate embodiment shown in FIGS. 8a and 8b, the topsheet 24 forms the permeable layer 52 similar to the previous embodiment, however, the impermeable layers 54a, 54b are disposed in two parallel Z-folds 90 formed in the topsheet 24 along the longitudinal length of the diaper 20. The Z-folded topsheet may be attached to the underlying layers along the longitudinal edges of the topsheet 24 allowing the center portion of the topsheet 24 to float freely. Elastic elements 92 are disposed along the outer edges of the impermeable layers 54a in order to deflect the center portion of the Z-folded topsheet outward away from the absorbent core 28. The combination of the Z-folded topsheet 24 and the elastic elements 92 maintains the temperature change elements in contact with the wearer's skin in the event that the diaper sags or fits loosely around the wearer.

Figure 9A:
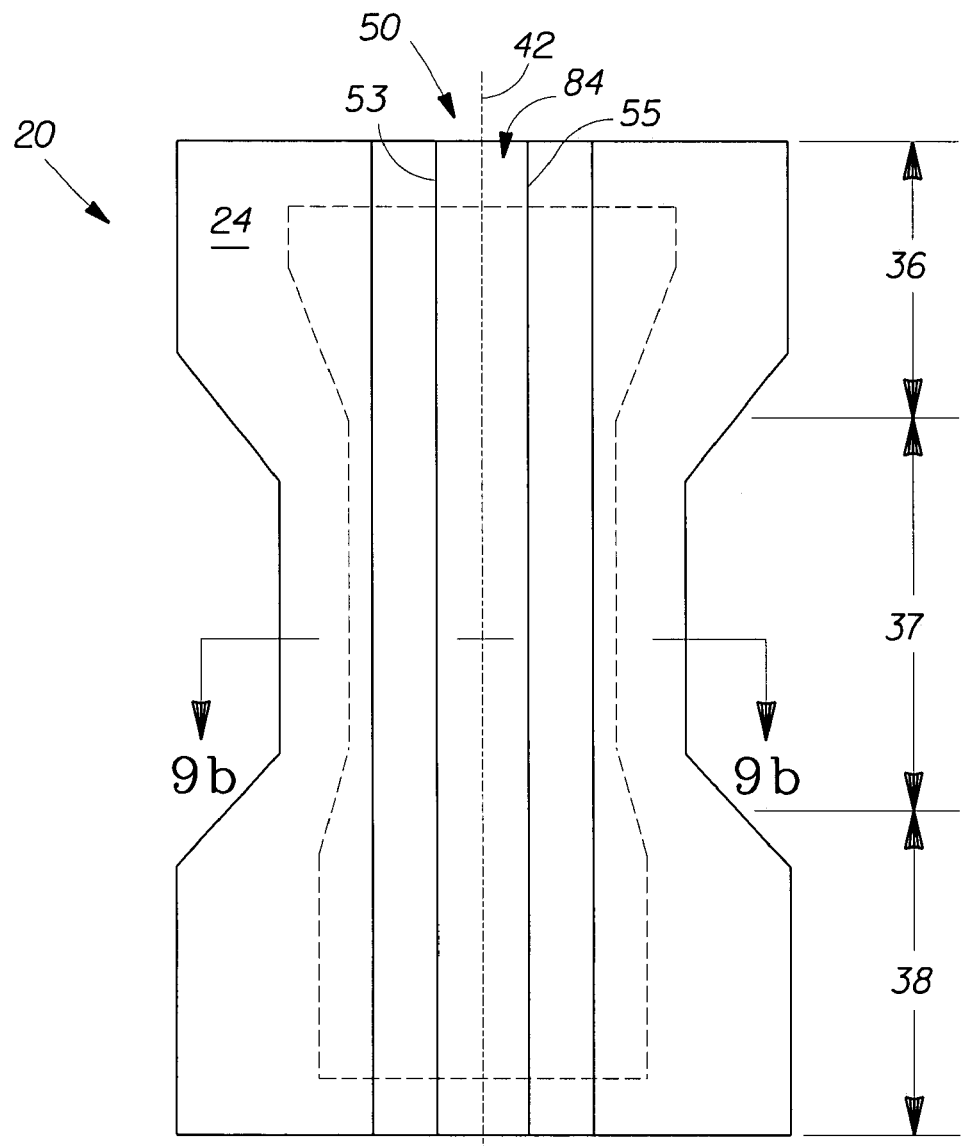
FIG. 9a is a plan view of a diaper having a temperature change element disposed on the body-facing surface wherein the temperature change element comprises a permeable layer partially enclosed by an impermeable layer.
Figure 9B:
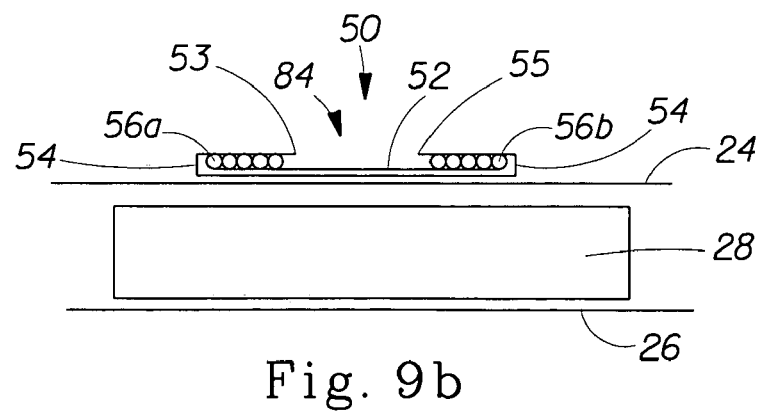

In another embodiment shown in FIGS. 9a and 9b, the temperature change element 50 includes a permeable layer 52 the majority of which is enclosed by an impermeable layer 54. For this embodiment, the impermeable layer 54 partially wraps around the permeable layer 52 such that the longitudinal edges 53, 55 of the impermeable layer 54 stop short of meeting, leaving a center portion 184 of the permeable layer exposed. The temperature change element 50 is preferably oriented such that the exposed center portion 84 is on the body-facing surface and aligned with the wearer's urethra. For this embodiment, the temperature change substance 56a and 56b is preferably disposed on the permeable layer away from the exposed center portion 84, preferably in two parallel regions covered by the longitudinal edges 53, 55 of the impermeable layer 54. During insults of urine, the exposed center portion 84 of the permeable layer 54 may wick the urine toward the temperature change substance 56a and 56b thereby wetting the substance and providing a signal to the wearer.

In addition to incorporating the temperature change element with the topsheet, the temperature change element of the present invention may also be integrated with other components of the diaper such as the barrier leg cuffs. The barrier leg cuffs may be made from either permeable or impermeable material. In either case, the barrier leg cuff material may form one of the layers of the temperature change element.

Figure 10A:
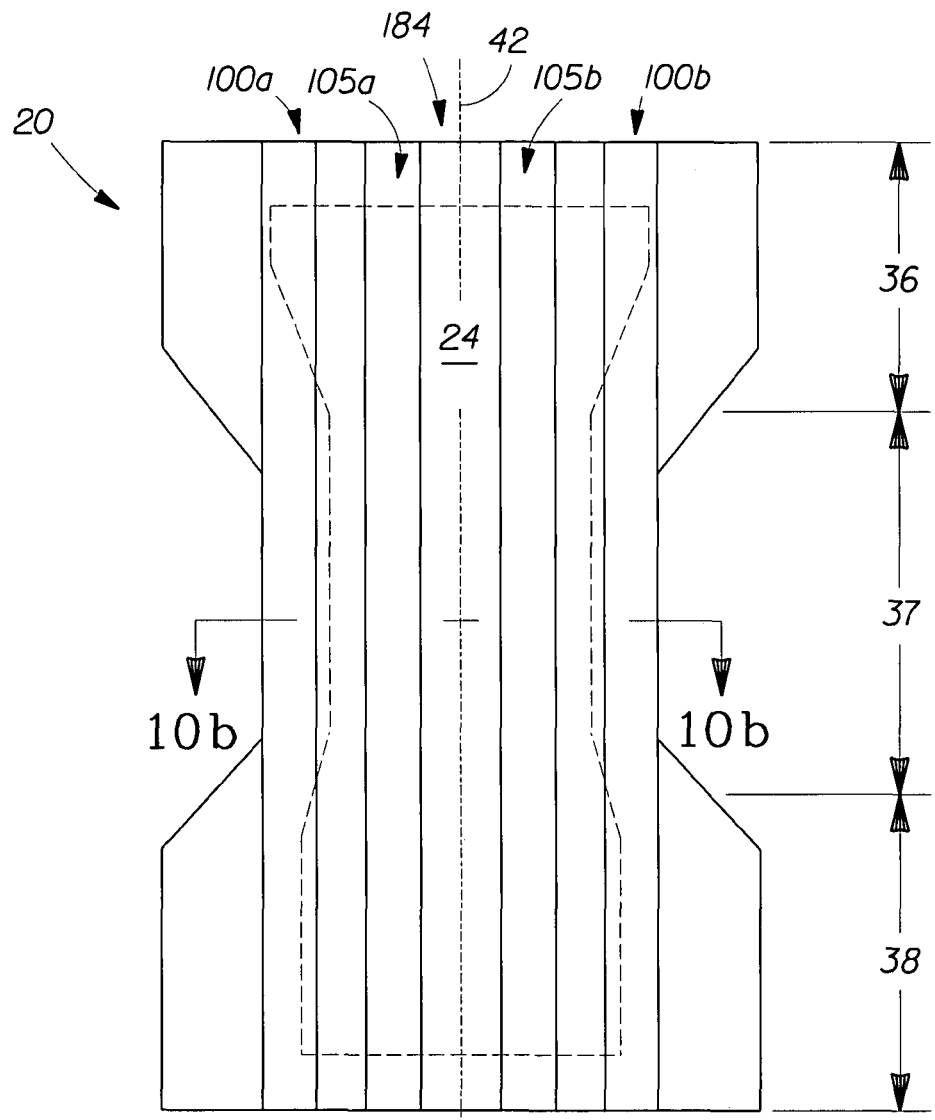
FIG. 10a is a plan view of a diaper with barrier leg cuffs including temperature change elements integrated with the leg cuffs.
Figure 10B:
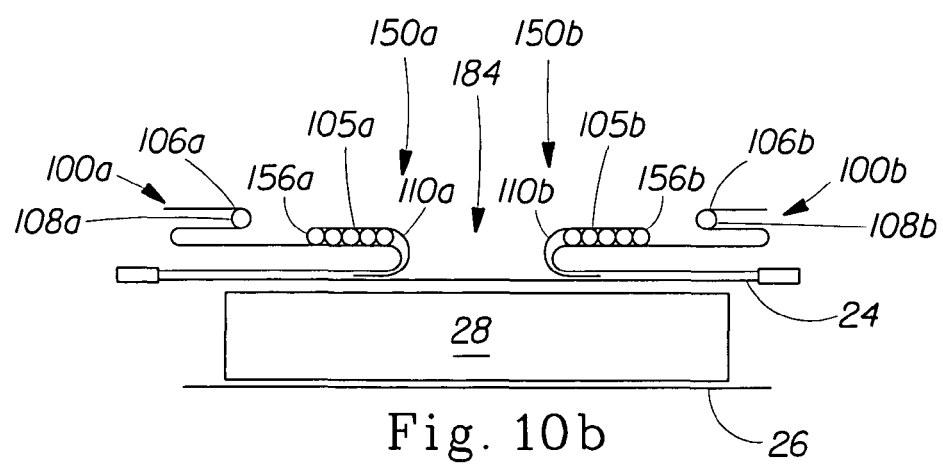

An example of temperature change elements integrated with the barrier leg cuffs is shown in FIGS. 10a and 10b. The diaper 20 for this embodiment includes barrier leg cuffs 100a, 100b made from impermeable material. The barrier leg cuffs 100a, 100b extend along the longitudinal edges of the diaper 20 in a parallel arrangement disposed on the body-facing surface of the topsheet 24 leaving an exposed center portion 184 of the topsheet 24 therebetween. For the embodiment shown in FIGS. 10a and 10b, temperature change elements 150a, 150b are incorporated with the barrier leg cuffs 100a, 100b such that the barrier leg cuff material provides the impermeable layer of the temperature change elements. A temperature change substance 156a and 156b is disposed on the body-facing surface of the barrier leg cuffs and covered by a separate permeable layer 110a and 110b of material. The temperature change substance 156a and 156b and the permeable layer 110a and 110b can extend the length of the barrier leg cuffs, preferably the length of the crotch region 37 and the front waist region 36, and are disposed on portions of the cuff closest to the longitudinal axis 42 of the diaper 20 to increase the likelihood of becoming wetted during urination. As shown in FIGS. 10a and 10b, the barrier leg cuffs 100a, 100b include Z-folded configurations with inner folds 105a, 105b disposed near the longitudinal axis 42 of the diaper 20 leaving a center portion 184 of the topsheet 24 exposed. The temperature change substance 156a and 156b is disposed on the inner folds 105a, 105b of the barrier leg cuffs 100a, 100b and covered with the permeable layer 110a and 110b. The Z-folded leg cuffs 100a, 100b also include outer folds 106a, 106b having elastic elements 108a and 108b disposed therein. During use, the elastic elements 108a and 108b deflect the leg cuffs away from the topsheet 24, towards the skin of the wearer.

The embodiments of temperature change elements disclosed hereunder perform effectively when held in contact with the skin of the wearer. In order to ensure that contact is made with the wearer's skin during use, the body facing portion of the temperature change elements may include a topical adhesive or body adhering composition which acts to hold the temperature change element in place during use. The topical adhesive may be applied to at least a portion of the body-facing surface of the temperature change element. However, the body adhering composition may also be integral with the material making up the body-facing layer of the temperature change element. Further, the body adhering composition may be disposed on any portion of the temperature change element contacting the skin of the wearer in any pattern or configuration including, but not limited to lines, stripes, dots, and the like.

Types of body adhering composition may include any one or more substances capable of releasably adhering to the skin of the wearer. Further, the body adhering composition may be in the form of a gel, lotion, film, web or the like. Examples of suitable body adhering compositions include adhesives, gelatin, petrolatum, waxes such as silicone or petroleum waxes, oils such as silicone or petroleum based oils, skin care compositions or ingredients thereof, as described below, and the like. Suitable topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699,146; 4,738,257; and 5,726,250; each of which is incorporated by reference herein.) The topical adhesives may also include any "medical adhesive" which is compatible for use with biological tissue, such as skin. Acrylic medical adhesives suitable for use as body adhering compositions include adhesives available from Adhesive Research, Inc., of Glen Rock, Pa., under the designations MA-46, MA-312, "MTTM" High MVTR adhesive, and AS-17. Rubber-based medical adhesives, such as SB-2 from Adhesive Research Inc. may also be suitable. Other exemplary adhesives include Dow Corning Medical Adhesive (Type B) available from Dow Corning, Midland, Mich.; "MEDICAL ADHESIVE" from Hollister Inc., of Libertyville, Ill.; 3M Spray Adhesives #79, 76, 77 and 90 available from the 3M Corp. of St. Paul, Minn.; and "MATISOL" liquid adhesive available from Ferndale Laboratories of Ferndale, Mich. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrrolidone and a multi-functional amine-containing polymer is disclosed in WO 94/13235A1. (The disclosure of each of these references is incorporated herein by reference.) Alternative body adhering means, which may be used in place of or in addition to those described above, include static electricity, suction, and the like. In any case, it is preferred that the body adhering composition permit vapors to pass (i.e., breathable), be compatible with the skin and otherwise skin friendly. Further, it is preferred that the body adhesive be at least partially hydrophobic, preferably 60%, more preferably 80%, by weight of the adhesive consist of hydrophobic components. However, hydrophilic adhesives are contemplated in certain embodiments of the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper having a longitudinal axis, a first waist region, a second waist region, and a crotch region interposed therebetween, the disposable diaper comprising:
    a backsheet;
    a permeable topsheet joined to the backsheet, the topsheet having an upper body-facing surface and a lower surface, wherein the permeable topsheet comprises two Z-folds parallel to the longitudinal axis;
    an absorbent core disposed intermediate the backsheet and the topsheet; and a plurality of temperature change elements disposed on the topsheet parallel to and spaced apart from the longitudinal axis, wherein the temperature change elements comprise permeable layers formed by the topsheet, impermeable layers formed by impermeable members disposed within the two Z-folds and interposed between the topsheet and the absorbent core, and a temperature change substance disposed on the topsheet, wherein urine deposited onto the temperature change elements can penetrate through the topsheet in a z direction to the impermeable members and wherein the impermeable members prevent urine from passing completely through the temperature change elements in the z direction and support the movement of urine in an x-y plane to wet the temperature change substance.

2. The disposable absorbent article as defined in claim 1, wherein the temperature change substance is interposed between the topsheet and the impermeable members.

3. The disposable absorbent article as defined in claim 1 wherein the impermeable members of the temperature change elements are elastically foreshortened.

4. The disposable absorbent article according to claim 1, wherein the two Z-folds further comprise two elastic members disposed along outside edges of the two impermeable members.

5. A disposable diaper having a longitudinal axis, a first waist region, a second waist region, and a crotch region interposed therebetween, the disposable diaper comprising:
    a backsheet;
    a topsheet joined to the backsheet;
    an absorbent core disposed intermediate the backsheet and the topsheet; and
    a temperature change element disposed on the topsheet along the longitudinal axis, the temperature change element includes a permeable layer having a body facing surface, a temperature change substance having a negative heat of solution and responsive to contact with urine to absorb heat and being disposed on the permeable layer, and an impermeable layer partially wrapped around the permeable layer such that longitudinal edges of the impermeable layer stop short of meeting, leaving a center portion of the body facing surface of the permeable layer exposed; and wherein the temperature change substance is disposed on the body-facing surface of the permeable layer in parallel regions covered by the longitudinal edges of the impermeable layer.

* * * * *

UNITED STATES PATENT AND TRADEMARK OFFICE
CERTIFICATE OF CORRECTION

| | |
|---|---|
| PATENT NO. | : 7,615,675 B2 |
| APPLICATION NO. | : 10/635249 |
| DATED | : November 10, 2009 |
| INVENTOR(S) | : Roe et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 801 days.

Signed and Sealed this

Nineteenth Day of October, 2010

David J. Kappos
*Director of the United States Patent and Trademark Office*